(12) United States Patent
Kim et al.

(10) Patent No.: US 11,744,664 B2
(45) Date of Patent: Sep. 5, 2023

(54) MEDICAL DRAPE

(71) Applicant: Man Yong Kim, Seoul (KR)

(72) Inventors: Man Yong Kim, Seoul (KR); Moung Keun Kim, Gunpo-si (KR)

(73) Assignee: Kim Man Yong, Seoul (KR)

(*) Notice: Subject to any disclaimer, the term of this patent is extended or adjusted under 35 U.S.C. 154(b) by 186 days.

(21) Appl. No.: 17/423,035

(22) PCT Filed: Oct. 14, 2020

(86) PCT No.: PCT/KR2020/013958
§ 371 (c)(1),
(2) Date: Jul. 14, 2021

(87) PCT Pub. No.: WO2022/010040
PCT Pub. Date: Jan. 13, 2022

(65) Prior Publication Data
US 2022/0338948 A1   Oct. 27, 2022

(30) Foreign Application Priority Data

Jul. 6, 2020 (KR) .......................... 20-2020-0002402

(51) Int. Cl.
| | | |
|---|---|---|
| A61B 46/20 | (2016.01) | |
| A61C 5/90 | (2017.01) | |
| A61B 46/00 | (2016.01) | |

(52) U.S. Cl.
CPC .............. *A61B 46/20* (2016.02); *A61B 46/40* (2016.02)

(58) Field of Classification Search
CPC ......... A61B 46/20; A61B 46/40; A41D 13/11; A61C 5/82; A61C 5/90

USPC .......................................................... 433/137
See application file for complete search history.

(56) References Cited

U.S. PATENT DOCUMENTS

| | | | | | |
|---|---|---|---|---|---|
| 420,876 | A | * | 2/1890 | Johson et al. ........... | A61C 5/82 433/136 |
| 1,604,136 | A | * | 10/1926 | Stoloff ..................... | A61C 5/82 433/137 |
| 1,774,285 | A | * | 8/1930 | Clay ........................ | A61C 5/82 433/137 |
| 3,406,452 | A | * | 10/1968 | McConville ............. | A61C 5/82 433/137 |
| 3,478,432 | A | * | 11/1969 | Gross ....................... | A61C 5/82 433/137 |
| 4,512,742 | A | * | 4/1985 | Shanel ..................... | A61C 5/82 433/136 |
| 4,626,211 | A | | 12/1986 | Coston | |

(Continued)

FOREIGN PATENT DOCUMENTS

| | | | | |
|---|---|---|---|---|
| EP | 2710976 A1 | 3/2014 | | |
| GB | 2 402 069 A | * | 12/2004 | ............... A61C 5/12 |

(Continued)

OTHER PUBLICATIONS

JP 2004 65882A translation.*

(Continued)

*Primary Examiner* — Camtu T Nguyen
(74) *Attorney, Agent, or Firm* — STIP Law Group, LLC

(57) ABSTRACT

Disclosed is herein a medical drape, and more particularly, a drape capable of preventing sprays generated from the mouth of a patient during dental treatment from being diffused by a first guard or the like to improve hygiene and fixation.

4 Claims, 5 Drawing Sheets

(56) References Cited

U.S. PATENT DOCUMENTS

| | | | | |
|---|---|---|---|---|
| 4,721,564 | A * | 1/1988 | Harada | A61M 1/3643 |
| | | | | 210/321.72 |
| 6,079,980 | A * | 6/2000 | Durand | A61C 5/90 |
| | | | | 128/206.13 |
| 6,185,740 | B1 | 2/2001 | Zegarelli et al. | |
| 2003/0028946 | A1 | 2/2003 | Zegarelli et al. | |
| 2004/0170945 | A1 * | 9/2004 | Heasley | A61C 5/82 |
| | | | | 433/136 |

FOREIGN PATENT DOCUMENTS

| | | |
|---|---|---|
| JP | 3110964 U | 7/2005 |
| JP | 3214805 U | 2/2018 |
| KR | 20090111413 A | 10/2009 |
| KR | 20150046875 A | 5/2015 |
| KR | 101629952 B1 | 6/2016 |

OTHER PUBLICATIONS

International search report of PCT/KR2020/013958, dated Mar. 29, 2021, English translation.
The extended European search report of EP 20 90 4297, dated May 23, 2023.

* cited by examiner

MEDICAL DRAPE

CROSS-REFERENCE TO RELATED APPLICATIONS

This application is the U.S. National Phase under 35 U.S.C. § 371 of International Application No. PCT/KR2020/013958 filed on Oct. 14, 2020, which in turn claims the benefit of Korean Application No. 20-2020-0002402 filed on Jul. 6, 2020, the disclosures of which are incorporated by reference into the present application.

BACKGROUND

Technical Field

The present disclosure relates to a medical drape and, more particularly, to a drape capable of preventing sprays generated from the mouth of a patient during dental treatment from being diffused by a first guard or the like to improve hygiene and fixation.

Background Art

A medical drape refers to a cloth in which, during a surgical operation or medical treatment, only a target region is open and surroundings thereof are covered. The medical drape is an essentially used medical supply that serves to block infection by preventing diffusion of sprays, foreign materials, etc. generated during a surgical operation or medical treatment and that can improve hygiene.

FIG. 1 is a schematic view illustrating a state in which a medical drape according to the present disclosure is used during dental treatment.

A hollow 11 is provided in a drape 10, and t drape 10 is positioned such that the hollow 11 is located around the mouth 1 of a patient. In this case, the drape 10 is generally positioned such that the nose 2 is located around the mouth 1 and the hollow 11 is located up to the nose 2 in order to facilitate breath of a patient.

However, the conventional drape 10 has the following problems.

First, because the drape 10 is placed around the mouth of a patient without a separate fixture, the drape 10 is displaced during dental treatment in many cases. For this reason, a treatment time is frequently delayed to set a position of the drape 10 again. There is a problem that a patient feels uncomfortable and fearful.

Further, sprays are generated from the mouth 1 of a patient during dental treatment, and a separate component capable of interrupting the sprays is not provided to the drape. For this reason, a problem that the sprays are splashed to the nose 2 adjacent to the mouth 1 of a patient or another bodily region occurs, which leads to a problem that a reduction in hygiene, an uncomfortable feeling of a patient, etc. caused by infection are generated.

Further, because the drape 10 is generally a cloth material, the sprays are absorbed to the cloth in many cases. In this case, after the sprays are absorbed to a bottom portion of the drape 10 which is in contact with the skin of a patient, the drape 10 and the skin of a patient are in continuous contact with each other, and thus there is a problem that a reduction in hygiene, an uncomfortable feeling of a patient, etc. are generated.

Therefore, a drape capable of improving hygiene and fixation of the drape 10 needs to be devised.

SUMMARY OF THE DISCLOSURE

The present disclosure is directed to providing a medical drape, and more particularly, to a drape capable of preventing diffusion of sprays, which are generated from the mouth of a patient during dental treatment, to improve hygiene and fixation.

To achieve the objective, a medical drape according to the present disclosure includes: a seat; an opening provided to be open to one point of the seat and located around a mouth of a patient; and a pair of catches provided to be separated from a bottom of the seat at a predetermined interval. The pair of catches are bindable to both ears of a patient to improve fixation of the seat.

Further, the medical drape according to the present disclosure further includes a first guard provided around the opening on the bottom of the seat, and the first guard prevents diffusion of sprays generated during dental treatment of a patient.

Further, the medical drape according to the present disclosure is configured such that an outer side of the first guard is rounded.

Further, each of the catches of the medical drape according to the present disclosure has a closed curve shape in which opposite ends thereof are coupled to the first guard.

In addition, the bottom of the seat of the medical drape according to the present disclosure is processed with a waterproof material.

According to the present disclosure, there is an advantage in that, due to first and second guards, diffusion of sprays generated during dental treatment can be prevented omnidirectionally, so that infection can be minimized, and hygiene can be maximized.

Further, there is an advantage in that, due to catches, fixation of a drape is improved.

BRIEF DESCRIPTION OF THE DRAWINGS

The above and other features of the present disclosure will now be described in detail with reference to certain exemplary embodiments thereof illustrated in the accompanying drawings which are given hereinbelow by way of illustration only, and thus are not limitative of the present disclosure, and wherein.

DETAILED DESCRIPTION

The present disclosure relates to a medical drape, and more particularly, to a drape capable of preventing diffusion of sprays, which are generated from the mouth of a patient during dental treatment, to improve hygiene and fixation.

Hereinafter, embodiments of the present disclosure will be described in detail so as to enable those having ordinary skill in the art to which the present disclosure pertains to extremely easily carried out them. However, the present disclosure may be implemented in various different forms and is not limited to the embodiments described here. Further, the present disclosure will be described below on the basis of a medical drape used during dental treatment.

Figure 1:
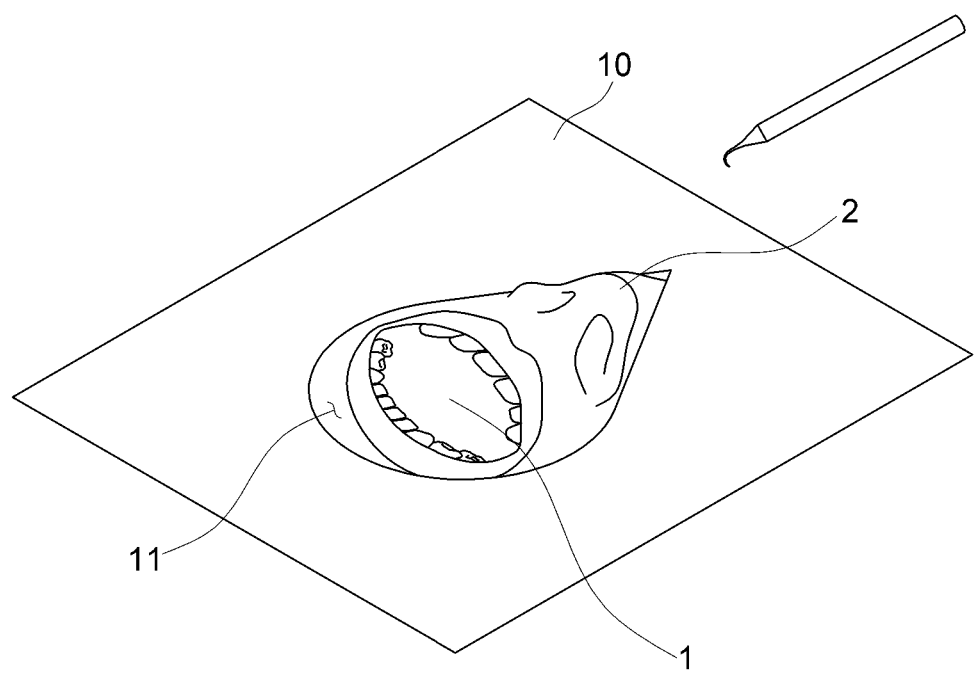
FIG. 1 is a schematic view illustrating a state in which a medical drape according to the present disclosure is used during dental treatment.
Figure 2:
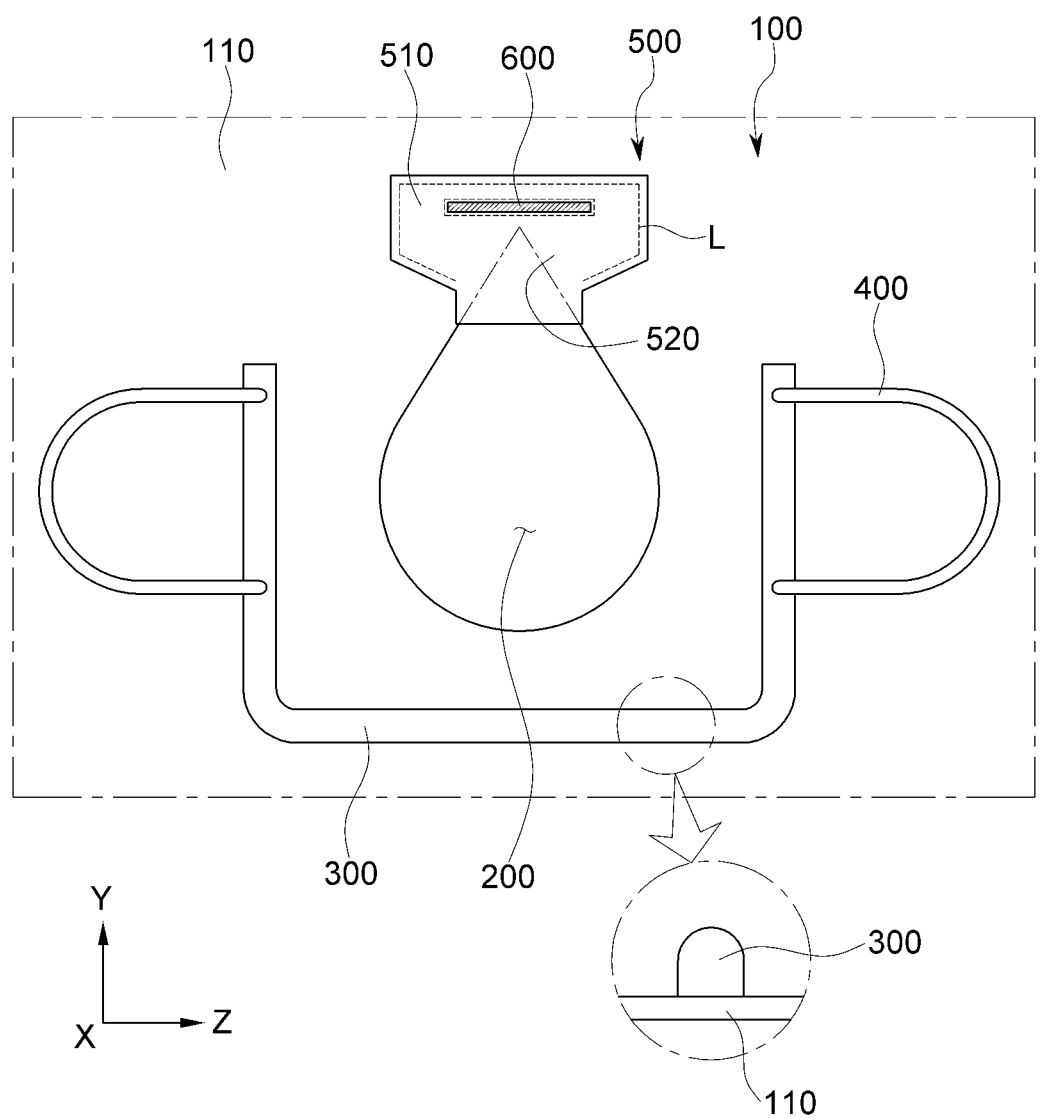
FIG. 2 illustrates a bottom of a medical drape according to the present disclosure.

FIG. 2 illustrates a bottom of a medical drape according to the present disclosure.

A medical drape according to the present disclosure includes a seat 100, an opening 200, a first guard 300, a catch 400, a second guard 500, and a wire 600.

The seat 100 covers surroundings of the mouth 1 and nose 2 of a patient. In FIG. 2, the seat is expressed in a rectangular shape, but is not limited to this shape. As described above in the related art, the seat 100 serves to prevent a spray, foreign materials, etc. from being splashed beyond a treatment part.

The seat 100 is divided into a bottom 110 and a front 120, and is preferably formed in two folds having different materials.

In this case, the bottom 110 of the seat 100 is preferably a waterproof material. When the bottom of the seat 100 is formed of a cloth that is a general material, if sprays, foreign materials, etc. are splashed on the seat 100 during treatment, the seat 100 comes into close contact with the skin of a patient with the sprays, foreign materials, etc. absorbed as they are, and thus a reduction in hygiene, an uncomfortable feeling, etc. may be caused. In the present disclosure, the bottom 110 of the seat 100 is treated with a waterproof material, and the spray, foreign materials, etc. are not absorbed by the seat 100 but flow down as they are, so that hygiene is improved to be able to reduce an uncomfortable feeling of a patient, and thus there is an advantage that can overcome conventional problems.

The opening 200 is provided in one spot of the seat 100. The opening is a hollow, and the mouth 1 and nose 2 of a patient are partly located in the hollow. For example, the opening 200 is preferably formed in a waterdrop form in order to prevent diffusion of the sprays and foreign materials.

Figure 3:
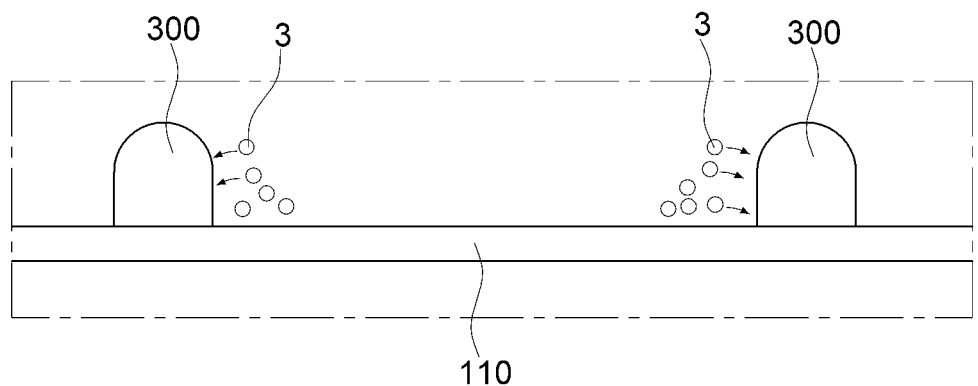
FIG. 3 is a view illustrating preventing diffusion of sprays when a first guard is viewed from the side.

The first guard 300 is provided around the opening 200 on the bottom 110 of the seat 100. The first guard 300 is described in detail with reference to an enlarged view of FIG. 2 and FIG. 3. FIG. 3 is a view illustrating preventing diffusion of sprays when a first guard is viewed from the side.

The first guard 300 is coupled to the bottom 110 of the seat 100. For example, the first guard 300 is preferably sewed on the bottom 110 of the seat 100. Further, the first guard 300 has a round outer surface, and preferably has a semicircular cross section. Further, the first guard 300 has a "U" shape when viewed from the bottom, and is preferably formed such that opposite ends thereof start from the cheeks adjacent to the ears in the face of a patient and wrap the jaw.

For this reason, it is possible to prevent diffusion of the spray (hereinafter referred to as foreign materials, all of which are also referred to as spays for convenience of description) generated in the dental treatment process of treating a tooth or a gum in the mouth 2. As illustrated in FIG. 3, the sprays 3 stay inside the first guard 300 due to the first guard 300 protruding from the bottom 110, so that the sprays 3 can be prevented from being diffused to the outside of the first guard 300.

Further, the "U" shape of the first guard 300 fundamentally interrupts most directions in which the sprays 3 can be diffused. On the basis of FIG. 2, all leftward, rightward, and downward directions of the diffusion are prevented by the first guard 300. In this case, in the case of an upward/downward direction, because the diffusion is prevented by the second guard 500 (to be described below), omnidirectional diffusion is prevented, thereby improving hygiene.

Further, the first guard 300 is formed to have a round outer surface, and thus there is an advantage that can minimize contact with the skin of a patient and minimize an uncomfortable feeling that gives a patient.

The catches 400 are provided on the bottom 110 of the seat 100 and are provided in a pair. Further, the pair of catches 400 are preferably located on opposite sides of the opening 200 so as to be separated at a predetermined interval. More preferably, when the drape is used, the catches 400 are preferably located round the ears of a patient. In this case, the catches 400 may be sewed between the first guard 300 and the seat 100, and are not necessarily limited thereto.

Each of the catches 400 has a ring shape, and opposite ends thereof are coupled to the first guard 300 or the bottom 110 of the seat 100. For this reason, a closed curve can be formed.

When the seat 100 is placed on the face of a patient, the pair of catches 400 are preferably shaped to be bindable to both the ears of a patient. That is, the catches 400 are caught on the ears of a patient in a mask earloop shape.

Therefore, contrast to placing the drape on the face of a patient in the related art, the catches 400 are caught on the ears of a patient, and thus fixation of the drape to the face of the patient is improved. For this reason, there is an advantage that can minimize a problem of treatment time delay caused by a change in position of the drape during treatment, and there is another advantage in that the drape comes into close contact with the face of a patient and diffusion of the spays 3 can be prevented.

Figure 7:
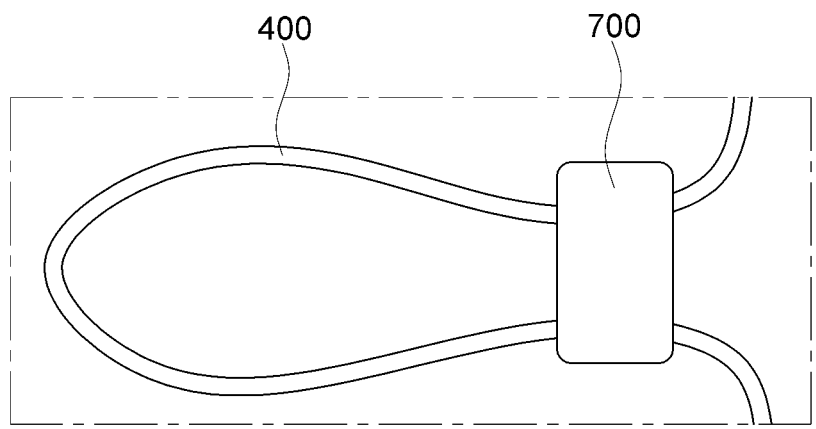
FIG. 7 illustrates an embodiment of the catch according to the present disclosure.

FIG. 7 illustrates another embodiment of the catch according to the present disclosure.

Another embodiment of the catch 400 further includes a tightener 700. One end and the other end of the catch 400 may pass through the tightener 700. To this end, through-holes (not illustrated) may be provided. Further, the tightener 700 may be, for instance, a plastic material, but is not limited thereto.

Therefore, the tightener 700 may be positioned to adjust a size of the area of the closed curve formed by the catch 400. On the basis of FIG. 7, the area becomes small when the tightener 700 is moved to the left, and becomes wide when the tightener 700 is moved to the right. Here, the area, namely a space, formed by the closed curve is a portion into which the ear of a patient is inserted, and may be set in a personalized form depending on the size of the ear of a patient. According to an embodiment, when the ear of a patient is much smaller than the area, the fixation of the drape is reduced. However, according to an embodiment, the area may be set in a personalized form, and there is an advantage in that the fixation of the drape is improved.

The second guard 500 is formed on the bottom 110 of the seat 100. Further, a part of the second guard 500 preferably protrudes to the opening 200.

When the drape covers the face of a patient, the second guard 500 preferably comes into contact with a periphery of the nose 2. Further, the second guard 500 is preferably sewed on the bottom 110 of the seat 100 (for example, a sewing line L is indicated in FIG. 2). In this case, the portion (whose reference sign is "520") of the second guard protruding to the opening 200 is not preferably sewed on the bottom 110 of the seat 100. For this reason, when the drape covers the face of a patient, a part of the second guard 500 can cover the nose 2 of a patient, and thus the diffusion of the sprays can be prevented.

Figure 4:
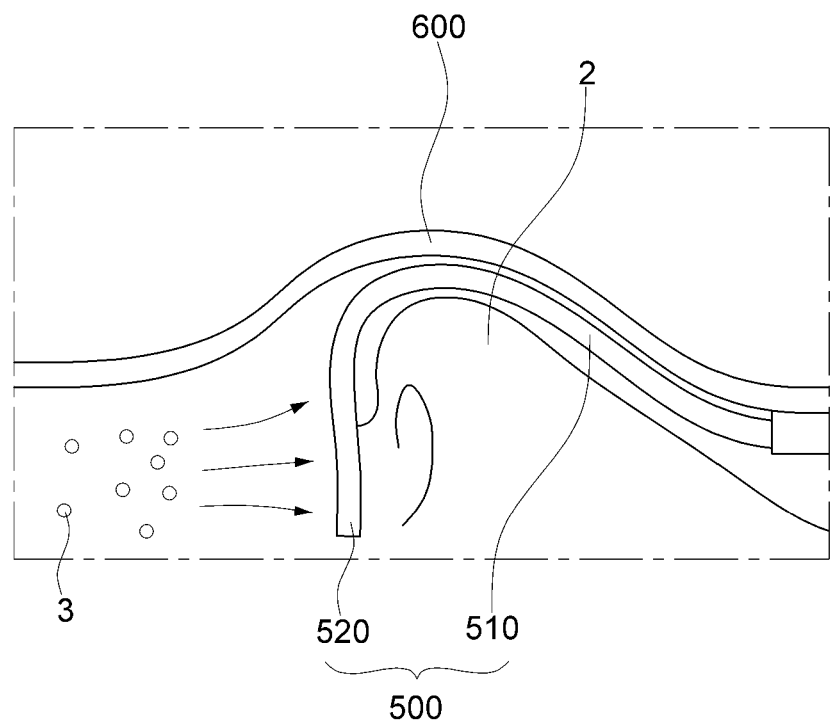
FIG. 4 is an enlarged side view illustrating a state in which a second guard covers the nose of a patient.
Figure 5:
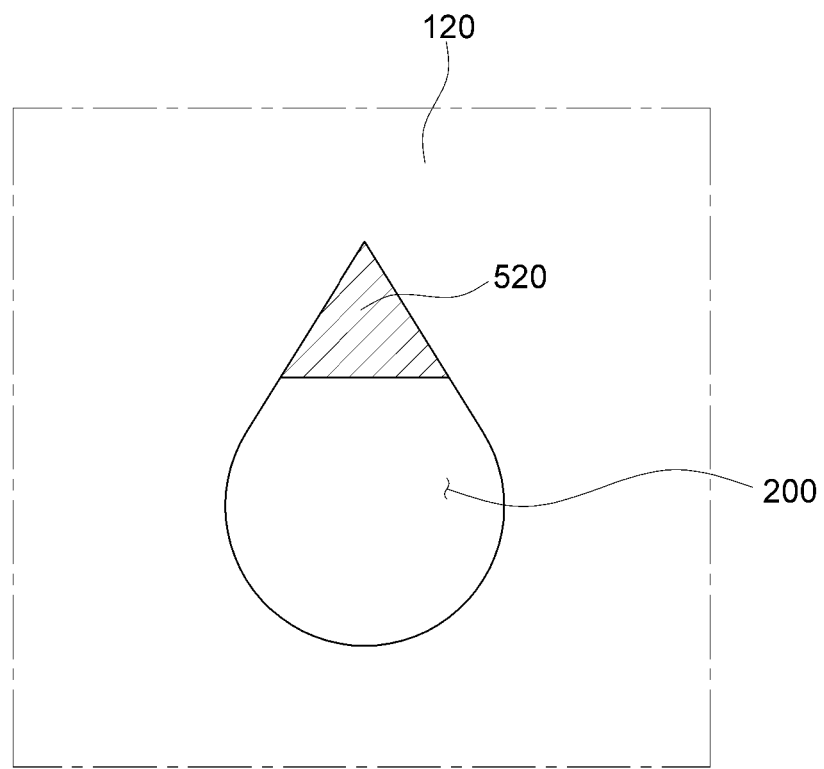
FIG. 5 illustrates a second guard part protruding to an opening.
Figure 6:
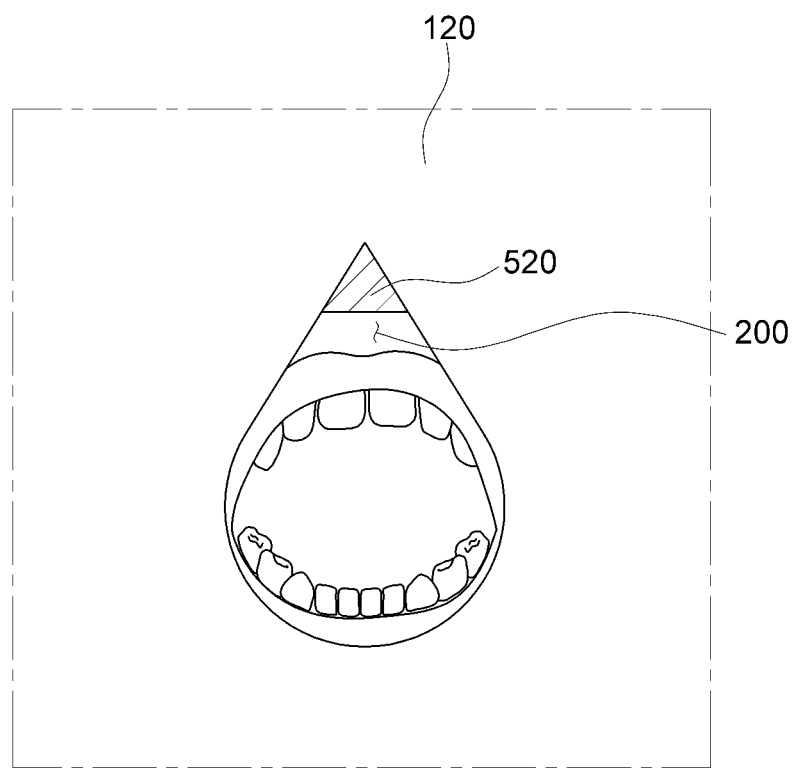
FIG. 6 is an enlarged front view illustrating a state in which the second guard part protruding to the opening covers the nose of a patient.

FIGS. 4 to 6 are views illustrating the above. FIG. 4 is an enlarged side view illustrating a state in which the second guard 500 covers the nose 200 of a patient. FIG. 5 is an enlarged view illustrating a second guard part 520 protruding to the opening 200, and FIG. 6 is an enlarged front view illustrating a state in which the second guard part 520 protruding to the opening 200 covers the nose 2 of a patient.

When the drape covers the face of a patient and a portion 510 of the second guard 500, which is sewed on the bottom 110 of the seat 100, wraps the nose 2 of a patient, opposite sides of the second guard part 520 protruding to the opening 200 are folded, and the second guard part 520 protruding to the opening 200 covers, as in FIG. 4, a nostril portion of the nose 2 of a patient.

In conclusion, the first guard 300 and the second guard 500 can prevent the omnidirectional diffusion of the sprays generated during dental treatment, and the hygiene is improved. Further, the second guard part 520 of the second guard 500 which protrude to the opening 200 does not come into close with, but is placed on the nostril portion of the nose 2 of a patient. This is because the second guard part is not sewed. Therefore, there is an advantage that can reduce an uncomfortable feeling of a patient who does not breathe.

The wire 600 is coupled to both the second guard 500 and the seat 100. The wire 600 is preferably a bendable soft wire type, and preferably extends in a longitudinal direction. Further, when the drape covers the face of a patient, the wire 600 is preferably disposed near the nostrils. For this reason, there is an advantage in that the fixation of the second guard 500 is improved and the entire drape comes into close contact with the face of a patient.

While preferred embodiments of the present disclosure have been described in detail, the scope of rights of the present disclosure is not limited thereto, but various modifications and improvements of those having ordinary skill in the art using basic concepts of the present disclosure defined in the claims to be described below also fall to the scope of rights of the present disclosure.

The present disclosure relates to a medical drape, and more particularly, to a drape capable of preventing diffusion of sprays, which are generated from the mouth of a patient during dental treatment, to improve hygiene and fixation.

What is claimed is:

1. A medical drape comprising:
   a seat;
   an opening extending through the seat and configured to surround a mouth of a patient;
   a pair of catches provided to be separated from a bottom of the seat at a predetermined interval; and
   a first guard provided around the opening on the bottom of the seat,
   wherein, the pair of catches configured to loop around both ears of the patient, and
   the first guard prevents diffusion of sprays which are generated from the mouth of the patient during dental treatment of the patient.

2. The medical drape of claim 1, wherein an outer side of the first guard is rounded.

3. The medical drape of claim 2, wherein each of the pair of catches has a curve-shaped and opposite terminating ends thereof; wherein each terminating end of said curve-shaped is coupled to the first guard so as each of the pair of catches forms a closed loop therewith.

4. The medical drape of claim 3, wherein the bottom of the seat is made by a waterproof material.

* * * * *